(12) United States Patent
Hale et al.

(10) Patent No.: US 8,963,110 B2
(45) Date of Patent: Feb. 24, 2015

(54) CONTINUOUS GENERATION OF EXTREME ULTRAVIOLET LIGHT

(71) Applicant: KLA-Tencor Corporation, Milpitas, CA (US)

(72) Inventors: Layton Hale, Castro Valley, CA (US); Francis Chilese, San Ramon, CA (US); Qiang Q. Zhang, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/309,393

(22) Filed: Jun. 19, 2014

(65) Prior Publication Data

US 2014/0374611 A1    Dec. 25, 2014

Related U.S. Application Data

(60) Provisional application No. 61/838,234, filed on Jun. 22, 2013.

(51) Int. Cl.
| | |
|---|---|
| *H01J 35/20* | (2006.01) |
| *H05G 2/00* | (2006.01) |
| *G01N 21/95* | (2006.01) |
| *G03F 7/20* | (2006.01) |

(52) U.S. Cl.
CPC .............. *H05G 2/008* (2013.01); *G01N 21/95* (2013.01); *G01N 21/9501* (2013.01); *G03F 7/70033* (2013.01)
USPC .............. 250/504 R; 250/492.1; 250/492.2; 250/493.1; 355/53; 355/67; 355/69

(58) Field of Classification Search
USPC ....... 250/504 R, 492.1, 492.2, 493.1; 355/53, 355/67, 69
See application file for complete search history.

(56) References Cited

U.S. PATENT DOCUMENTS

| | | |
|---|---|---|
| 2008/0165415 A1 | 7/2008 | Chan et al. |
| 2008/0197298 A1 | 8/2008 | Abe et al. |
| 2008/0210889 A1 | 9/2008 | Suganuma et al. |
| 2009/0314967 A1 | 12/2009 | Moriya et al. |
| 2011/0141446 A1 | 6/2011 | Walser et al. |
| 2012/0050706 A1* | 3/2012 | Levesque et al. ............... 355/55 |

OTHER PUBLICATIONS

Mochizuki, T, "Laser plasma X-ray source by cryogenic target and high rep rate slab YAG laser", Proc. SPIE 3886, High-Power Lasers in Energy Engineering, 306, Jan. 11, 2000.*

* cited by examiner

*Primary Examiner* — Jack Berman
*Assistant Examiner* — Meenakshi Sahu
(74) *Attorney, Agent, or Firm* — Suiter Swantz pc llo

(57) ABSTRACT

The generation of EUV light includes rotating a cylinder at least partially coated with a plasma-forming target material, directing pulsed illumination to a first set of helically-arranged spots traversing a material-coated portion of the rotating cylinder in a first direction and directing pulsed illumination to a second set of helically-arranged spots traversing the material-coated portion of the rotating cylinder in a second direction, the pulsed illumination being suitable for exciting the plasma-forming target material.

30 Claims, 7 Drawing Sheets

CONTINUOUS GENERATION OF EXTREME ULTRAVIOLET LIGHT

PRIORITY

The present application claims priority under 35 U.S.C. §119(e) to U.S. Provisional Patent Application Ser. No. 61/838,234, titled EXPOSURE PATTERN FOR UNINTERRUPTED EUV GENERATION FROM A SPINNING CYLINDER METHOD, NOT APPARATUS, by Layton Hale et al., filed Jun. 22, 2013, or is an application of which currently co-pending application(s) are entitled to the benefit of the filing date. The above-referenced provisional patent application is hereby incorporated by reference in its entirety.

TECHNICAL FIELD

The present disclosure generally relates to the field of illumination systems and, more particularly, to plasma-based illumination systems.

BACKGROUND

As the demand for lithography-based device structures having ever-smaller features continues to increase, the need for improved illumination sources used for inspection of the associated reticles that lithographically print these ever-shrinking devices continues to grow. One such illumination source includes an extreme ultraviolet (EUV) light source. One method of creating EUV light includes spinning a cylinder coated with a uniformly thick layer of solid (frozen) plasma-forming target material, such as xenon, and exposing the xenon-coated portion of the cylinder with a pulsed laser suitable for exciting the xenon to generate plasma. In addition, prior to the next pulse of illumination, the cylinder must be rotated and/or translated to expose a fresh region of solid xenon. As the cylinder rotates, gaseous xenon may be sprayed onto the cold non-illuminated portion of the surface of the cylinder, reforming the frozen xenon layer at previously-illuminated spots in order to fill the portions of the xenon ice consumed by the laser over time. A particular spot or zone is not exposed again until sufficient time has elapsed, allowing for the solid xenon surface to return to its original condition. Adjacent spots must be separated by some minimum distance in order to prevent damage to the cylinder surface.

The plasma creation takes place in a fixed location because the associated collection optics must be arranged around a known location and cannot "slew" around to follow a moving plasma source, which would cause mirror distortion. The need for the plasma to appear in a fixed location prevents the use of a moving illuminator laser spot. This creates a challenge in applications involving EUV light sources. To allow maximum operational time and inspection uniformity, a reticle inspection tool should have a source of pulsed EUV light that is not interrupted, but rather runs at a chosen pulse frequency for a long period of time (e.g., hours), which is required to inspect a reticle.

The creation of EUV light using solid xenon on a rotating cylinder has generally been accomplished with two methods. First, the cylinder, rotating at a constant speed, moves slowly in the axial direction from one end to the other, creating a helix of spots along the cylinder. When the helix intersects the top of the usable length of the xenon ice, the illuminating laser is blocked or turned off until the cylinder is moved back to the other end of travel. The total length of time for the helix of exposure plus the retrace time must be sufficient to allow the xenon ice to reform. In the second method, the pulse rate of the illumination laser is held low enough and/or the cylinder is of a large enough diameter that the spots can overlap after one revolution (e.g., forming a single ring around the cylinder at one axial location).

These methods have several deficiencies, especially as applied to generation of uninterrupted EUV illumination. The first method requires the illumination source to be blocked periodically (on the order of every few seconds). This may force, for example, a reticle inspection machine to stop inspecting and then restart after the cylinder is reset, impacting stability and creating overlay issues. The second method requires either a very low pulse rate, which may cause unacceptably long inspections of a reticle, or a very large diameter cylinder, which may cause mechanical vibration instability issues, or both. Therefore, it is desirable to provide a method and system that cure the defects of the prior art identified above.

SUMMARY

A method of generating a continuous or near-continuous EUV light output is disclosed, in accordance with one illustrative embodiment of the present disclosure. In one embodiment, the method includes rotating a cylinder at least partially coated with a plasma-forming target material; directing pulsed illumination to a first set of helically-arranged spots traversing a material-coated portion of the rotating cylinder in a first direction; and directing the pulsed illumination to a second set of helically-arranged spots traversing the material-coated portion of the rotating cylinder in a second direction, the pulsed illumination being suitable for exciting the plasma-forming target material. As the first and second sets of helically-arranged spots are exposed during a first helical probe up/down the cylinder and a second helical probe down/up the cylinder, enough time passes for reformation of target material over the previously-probed spots so that the process can be repeated without interruption.

A system generating a continuous or near-continuous EUV light output is disclosed, in accordance with one illustrative embodiment of the present disclosure. In one embodiment, the system may include a rotatable, cylindrically-symmetric element at least partially coated with plasma-forming target material; a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; and one or more collection optical elements configured to receive illumination emanated from a plasma generated in response to the excitation of the plasma-forming target material and further configured to direct the illumination towards an intermediate focal point. As discussed in further detail below, one or more actuators may be controlled to axially and/or rotationally accelerate the cylinder in order to perform a phase shift at the ends of the exposure pattern, so the alignment of the pulsed illumination can be shifted from the first set of helically-arranged spots to the second set of helically-arranged spots or vice versa.

An optical inspection system is disclosed, in accordance with one illustrative embodiment of the present disclosure. In one illustrative embodiment, the optical inspection system includes an illumination sub-system. In one illustrative embodiment, the illumination sub-system includes a rotatable, cylindrically-symmetric element at least partially coated with plasma-forming target material; a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; one or more collection optical elements configured to collect illumination emanated from a plasma generated in response to the excitation of the plasma-forming target material; and a set of illuminator optics configured to direct illumination from the one or more collection optical elements to one or more specimens. In another illustrative embodiment, the optical inspection system includes a detector and a set of projection optics configured to receive illumination from the surface of the one or more specimens and direct the illumination from the one or more specimens to the detector.

An optical lithography system is disclosed, in accordance with one illustrative embodiment of the present disclosure. In one illustrative embodiment, the optical lithography system includes an illumination sub-system. In one illustrative embodiment, the illumination sub-system includes a rotatable, cylindrically-symmetric element at least partially coated with plasma-forming target material; a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; and one or more collection optical elements configured to collect illumination emanated from a plasma generated in response to the excitation of the plasma-forming target material. In one illustrative embodiment, the optical lithography system includes a set of illuminator optics configured to direct collected illumination to a mask. In another illustrative embodiment, the optical lithography system includes a set of projection optics configured to receive illumination reflected from the mask and direct the reflected illumination from the mask to one or more wafers.

A method of continuously or near-continuously probing an information- or material-bearing cylindrically-symmetric element is disclosed, in accordance with one illustrative embodiment of the present disclosure. In one illustrative embodiment, the method may be applied to read/write patterning for data storage systems including cylindrical storage mediums or chemical exposure patterning for applications with material coated cylinders. In another illustrative embodiment, the method may include rotating the cylinder, probing a first set of helically-arranged spots traversing an information- or material-bearing portion of the rotating cylinder in a first direction, and probing a second set of helically-arranged spots traversing the information- or material-bearing portion of the rotating cylinder in a second direction.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 4 generally illustrate embodiments of a system and method for generating continuous or near-continuous plasma-based illumination output, in accordance with one embodiment of the present invention.

Embodiments of the present disclosure are directed to the exposure of a rotating cylindrically-symmetric element (e.g., cylinder) in an uninterrupted pattern by an illumination source (e.g., pulsed laser) and the reconditioning of plasma-forming regions on the cylinder surface (e.g., reconditioned via application of new material). In the case of plasma-based illumination (e.g., EUV light), the cylindrically-symmetric element provides a stable, uniform solid plasma-forming material surface (e.g., xenon surface) without unnecessarily enlarging the cylinder. Embodiments of the present disclosure provide for an uninterrupted exposure pattern, achieved via judicious combinations of rotational and axial movements and accelerations. For example, embodiments of the present invention are directed to the combination of rotational and axial acceleration of a cylindrically-symmetric element bearing a plasma-forming material (e.g., suitable for EUV generation) and proper spacing to accommodate a first helical pattern and a return second helical pattern. Additional embodiments of the present disclosure provide for a reticle inspection system, a wafer inspection system or a lithography system (or other optical system) incorporating the plasma-based rotating cylinder source described herein.

Figure 1:
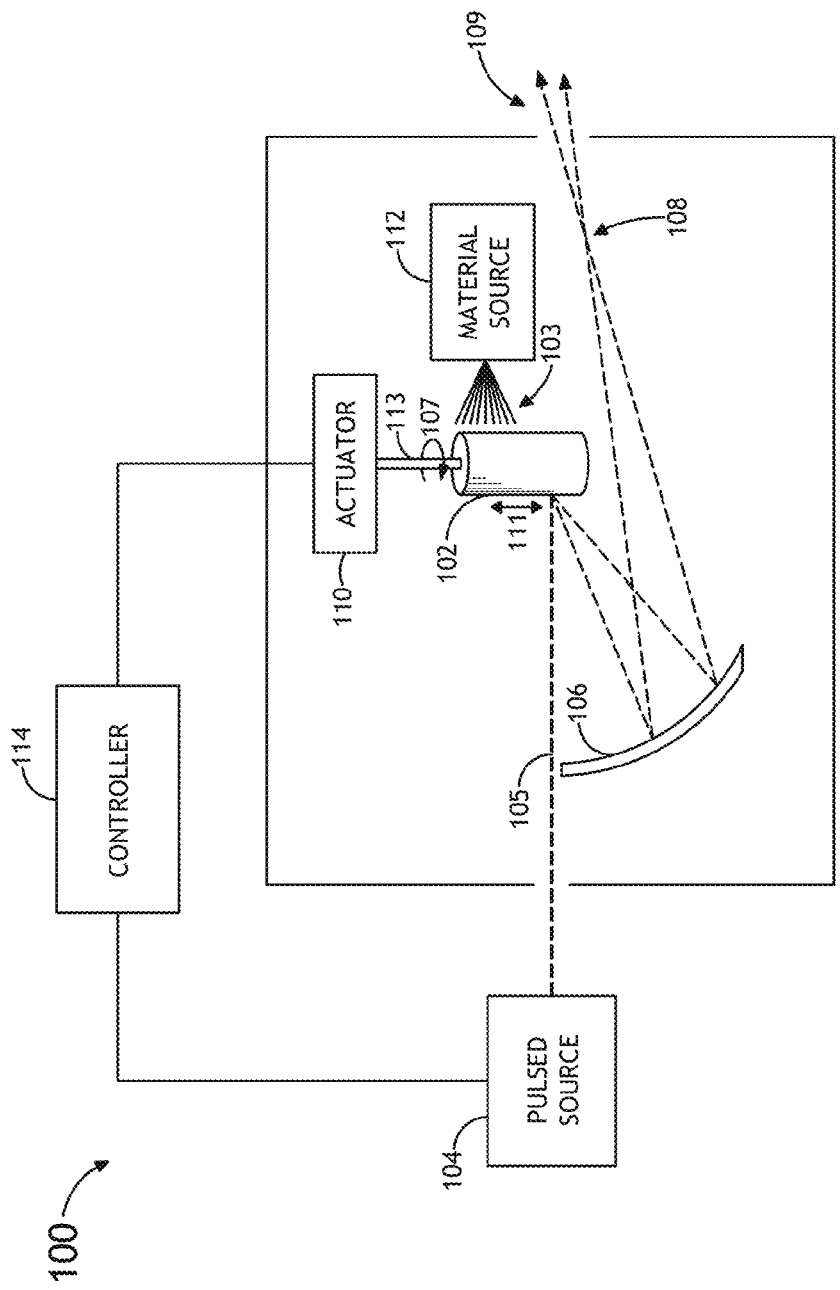
FIG. 1 is a block diagram illustrating a system for generating plasma-based illumination by exciting plasma-forming target material coated on a rotating cylinder, in accordance with an embodiment of this disclosure.

FIG. 1 illustrates a block diagram view of a system 100 for generating a continuous or near-continuous plasma-based illumination output, in accordance with one or more embodiments of the present disclosure.

In one embodiment, the system 100 includes a rotatable, cylindrically-symmetric element 102. In one embodiment, the rotatable, cylindrically-symmetric element 102 is suitable for rotation about an axis. In one embodiment, the rotatable, cylindrically-symmetric element 102 includes a cylinder, as shown in FIG. 1. In other embodiments, the rotatable, cylindrically-symmetric element 102 includes any cylindrically symmetric shape in the art. For example, the rotatable, cylindrically-symmetric element 102 may include, but is not limited to, a cylinder, a cone, a sphere, an ellipsoid and the like. Further, the cylindrically-symmetric element 102 may include a composite shape consisting of two or more shapes. It is noted herein that for the purposes of descriptive convenience the system 100 and related embodiments are described in the context of a rotatable or rotating cylinder 102, as depicted in FIG. 1, however this should not be interpreted as a limitation on the present invention.

In another embodiment, the rotatable cylinder 102 is at least partially coated with a plasma-forming target material 103. The plasma-forming target material 103 may include any material known in the art that generates plasma when excited by an illumination source. For example, the target material 103 may include, but is not limited to, xenon. In another embodiment, the target material 103 may include a solid material disposed on the surface of the rotatable cylinder 102. For example, the target material 103 may include, but is not limited to, xenon frozen onto the surface of the rotatable cylinder 102.

In one embodiment, the system 100 includes a material source 112. In one embodiment, the material source 112 contains material used to coat the rotatable cylinder 102. For example, the material source 112 may be used to apply a selected material to the surface of the rotatable cylinder 102. In one embodiment, the material source 112 may direct a gas or liquid stream or spray onto the surface of the cylinder 102 as it rotates, and is maintained at a temperature below the freezing point of the selected material. For example, the selected material may include, but is not limited to, xenon and like materials. For instance, the rotatable cylinder 102 may be cooled below the xenon freezing point (e.g., −111.8° C.). Then, xenon may be applied to the surface of the rotatable cylinder 102 causing the xenon to freeze onto the surface of the rotatable cylinder 102 as it is rotated, thereby forming a solid xenon layer on the surface of the cylinder 102. In one embodiment, the rotatable cylinder 102 may include an internal reservoir for containing a coolant material. For example, in the case of xenon, the rotatable cylinder 102 may include an internal reservoir holding a volume of liquid nitrogen used to cool the applied xenon below the freezing point for xenon.

In another embodiment, the system 100 may include a mechanism used to improve the quality of the layer of plasma-forming material on the cylinder 102. In one embodiment, the system 100 may include a thermal device and/or a mechanical device located outside of the cylinder 102 suited to aid in forming (or maintaining) a uniform layer of the plasma-forming material on the surface of the cylinder 102. For example, in the case of xenon, the system 100 may include, but is not limited to, a heating element arranged to smooth or control the density of the xenon ice layer formed on the surface of the cylinder 102. By way of another example, in the case of xenon, the system 100 may include, but is not limited to, a blade device arranged to smooth or control the density of the xenon ice layer formed on the surface of the cylinder 102.

As discussed in greater detail further herein, the material source 112 may also serve to 'recoat' one or more portions of the cylinder 102.

In another embodiment, the system 100 includes a pulsed illumination source 104. The pulsed illumination source 104 may include any pulsed or modulated illumination source known in the art. For example, the pulsed source 104 may include, but is not limited to, a pulsed laser. Further, the pulsed illumination source is suitable for initiating and/or maintaining a plasma in the material 103. For example, the pulsed illumination source 104 may include, but is not limited to, one or more infrared (IR) lasers. For instance, the pulsed illumination source 104 may include, but is not limited to, one or more $CO_2$ lasers.

Figure 2:
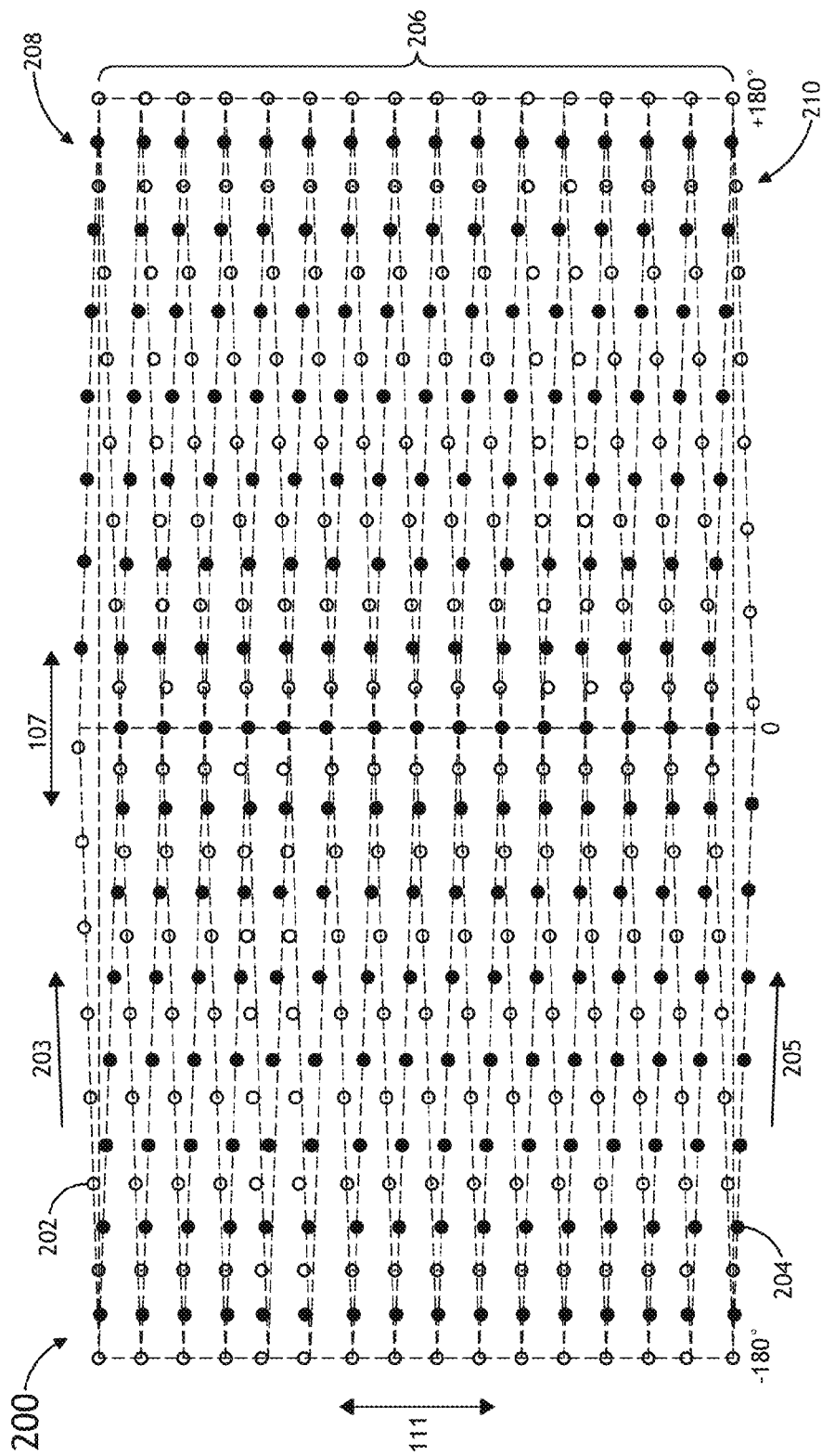
FIG. 2 is a conceptual illustration of an exposure or probing pattern on a surface of a cylinder, wherein the exposure pattern includes a first set of helically-arranged spots traversing the cylinder in a first direction and a second set of helically-arranged spots traversing the cylinder in a second direction, in accordance with an embodiment of this disclosure.

FIG. 2 illustrates a conceptual view 200 of a first set of illumination spots and a second set of illumination spots distributed across the surface of the cylinder 102, in accordance with one embodiment of the present invention. In one embodiment, as the rotatable cylinder 102 is rotated, the pulsed illumination source 104 directs pulsed illumination 105 to a first set of spots 202 traversing a material-coated portion of the cylinder 102 in a first direction 203. In another embodiment, as the rotatable cylinder 102 is rotated, the pulsed illumination source 104 directs pulsed illumination 105 to a second set of spots 204 traversing the material-coated portion of the cylinder 102 in a second direction 205. In one embodiment, the first set of spots 202 and the second set of spots 204 each form a helical pattern about the surface of the rotating cylinder 102, noting that the surface depicted in FIG. 2 is representative of a cylindrical surface spanning −180° to +180° about the axis of the cylinder along the rotational direction 107. In one embodiment, the cylinder 102 may be translated at a constant velocity in the overlap region 206 along the axial direction 111. In another embodiment, the cylinder 102 may be decelerated/accelerated in the transitional regions 208, 210.

In one embodiment, the first set 202 of helically-arranged spots is arranged so as not to overlap with the second set 204 of helically-arranged spots, as shown in FIG. 2. In one embodiment, the first set 202 of helically-arranged spots and/or the second set 204 of helically-arranged spots consist of spots that are spaced at least twice as far apart in the circumferential direction 107 as a predetermined threshold spacing, while being spaced in the axial direction 111 at a distance equal to that threshold spacing. In another embodiment, the threshold spacing is the minimum distance between adjacent spots required to avoid exposure of non-targeted portions of the rotating cylinder 102 by the pulsed illumination 105. It is noted herein that the factor of two used above is not a limitation on the present invention and should be interpreted merely as illustrative. It is recognized herein that the actual spacing used between spots may consist of any factor of the minimum distance between adjacent spots necessary to avoid exposure of non-target portions of the rotating cylinder 102 by pulsed illumination. For example, the factor may include any number in the range 1-4.

It is recognized herein that the threshold spacing is dependent upon one or more of the following: the size of the surface of the cylinder damaged/removed by the pulsed illumination, rotational speed of the rotating cylinder, diameter of the rotating cylinder, the pulse-rate of the pulsed illumination, the length of the material-coated portion of the rotating cylinder, and the deposition rate of the plasma-forming target material upon the cylinder.

In another embodiment, the system 100 includes an actuator 110 configured to actuate the rotatable cylinder 102. In one embodiment, the actuator 110 includes a linear actuator configured to translate the rotatable cylinder 102 along an axial direction 111. For example, the rotatable cylinder 102 may be coupled to the actuator 110 via shaft 113. It is recognized herein that the present invention is not limited to the actuator 110. As such, the description provided above should be interpreted merely as illustrative. For instance, the pulsed source 104 may be disposed on an actuating stage (not shown), which provides translation of the beam 105 relative to the cylinder 102.

The axial motion imparted by the actuator 110 and the rotational motion of the cylinder 102 allows for tracing of the pulsed illumination 105 in a set of helical patterns across the surface of the cylinder, corresponding with the first set of spots 202 and the second set of spots 204 described previously herein. In this regard, the first set of spots 202 may form a first helical pattern during rotational and axial acceleration of the cylinder 102, while the second set of spots 204 form a return second helical pattern that avoids overlapping the first pattern.

In another embodiment, the system 100 includes a controller 114 communicatively coupled to the actuator 110 and/or pulsed source 104. In one embodiment, the controller 114 controls the actuation of the rotatable cylinder 102 along an axial direction 111 relative to the pulsed source 104. In another embodiment, the controller 114 controls the pulsed source 104 (e.g., pulse timing, direction and etc.). In this regard, the controller 114 may direct the actuator 110 and the cylinder 102 to trace the pulsed illumination 105 across the surface of the cylinder, as the cylinder rotates, in any manner described in the present disclosure.

In one embodiment, the controller 114 may direct the actuator 110 to axially actuate the rotating cylinder 102 relative to the pulsed illumination source 104 so to direct the pulsed illumination 105 to the first set of helically-arranged spots 202 traversing the material-coated portion of the rotating cylinder 102 in the first direction 203. In another embodiment, the controller 114 may direct the actuator 110 to axially actuate the rotating cooled cylinder 102 relative to the pulsed illumination source 104 so to direct the pulsed illumination 105 to the second set 204 of helically-arranged spots traversing the material-coated portion of the rotating cylinder 102 in the second direction 205.

In another embodiment, during a change from the first direction of the pulsed illumination to the second direction of the pulsed illumination, the controller 114 may control the rotational speed and/or the axial speed of the rotating cylinder 102 in order to phase shift an illumination pattern of the pulsed illumination 105 from being aligned with the first set of helically-arranged spots 202 to being aligned with the second set of helically-arranged spots 204. In this regard, the controller 114 may direct the rotating cylinder and/or actuator 110 to shift the cylinder 102 from the first helical pattern to a second return helical pattern and vice-versa.

In another embodiment, the material source 112 is configured to recoat portions of the rotatable cylinder with the plasma-forming material 103. In one embodiment, the material source 112 is configured to recoat previously-illuminated portions of the rotatable cylinder 102 with the plasma-forming material 103. For example, the material source 112 may recoat spots previously 'hit' with illumination 105 with a plasma-forming material, such as, but not limited to, xenon. Further, the length of the cylinder 102 and the axial speed of the cylinder 102 may be selected so as to provide ample time for the plasma-forming material (e.g., xenon) to solidify on the cylinder 102 before the next illumination exposure.

In one embodiment, once the threshold distance between adjacent spots (e.g., spots 202 or spots 204) is determined, the size and rotational speed of the cylinder 102 are selected so as to place adjacent spots at a distance twice that of the threshold distance in the circumferential direction 107. In another embodiment, an axial speed is chosen so as to place adjacent spirals of the helix to be formed at a distance substantially equal to the determined threshold distance. In another embodiment, the helical pattern is maintained at a constant rotational speed and upward axial speed until the cylinder 102 is approximately a threshold distance away from the end of its useful travel. At that point, the cylinder 102 begins its acceleration downward. In another embodiment, the acceleration rate is chosen so that the acceleration needed to reach the desired downward speed is completed in substantially one 360° rotation of the cylinder 102. In another embodiment, during this downward axial acceleration period, the cylinder rotation speed is increased and then decreased so that, by the time the axial acceleration is complete, the cylinder rotation will have advanced a distance equal to the threshold distance. In another embodiment, the rotational speed is held constant as the cylinder 102 moves downward. In another embodiment, the helical pattern of spots created on the way down falls in between the rotational location of the spots that were created on the upward stroke. It is noted herein that the spacing of adjacent spots along the rotational direction by two times the threshold distance provides for 'extra spacing,' allowing the spots to interleave without violating the threshold distance. In another embodiment, at the bottom of the travel, the process is reversed and the upward spiral begins again. In another embodiment, the cylinder length is determined to ensure adequate time has elapsed during the upward and then downward motion so the spots previously-exposed by the illumination 105 have been completely reformed with solid plasma-forming material (e.g., xenon). By way of example, an adjacent spot separation in the range of 0.5 to 1.0 mm may be adequate for the purposes of the present invention. By way of another example, a pulse repetition frequency for the pulsed illumination 105 of 1-10 kHz may be adequate for the purposes of the present invention. By way of another example, the time required to reform a plasma-forming solid (e.g., xenon ice) at a previously-exposed spot on the cylinder 102 may include up to 20 seconds. It is recognized herein that the above values are not limitations and are provided merely for illustrative purposes.

In another embodiment, the system 100 includes one or more collection optical elements 106 arranged to collect plasma-based illumination emanating from the plasma-formed regions on the cylinder 102. For example, after light is generated by the plasma excited by the pulsed source 104, the light may then be collected by collector 106. For example, the collector 106 may include any collector known in the art. For instance, the collector 106 includes any collector known in the art compatible with EUV light. In another embodiment, the collection optics 106 may direct and/or focus illumination 109 emanating from the cylinder 102 to one or more downstream optical elements. In another embodiment, the collection optics 106 may be configured to focus illumination emanating from the cylinder 102 to an intermediate focus 108, as shown in FIG. 1.

Figure 3:
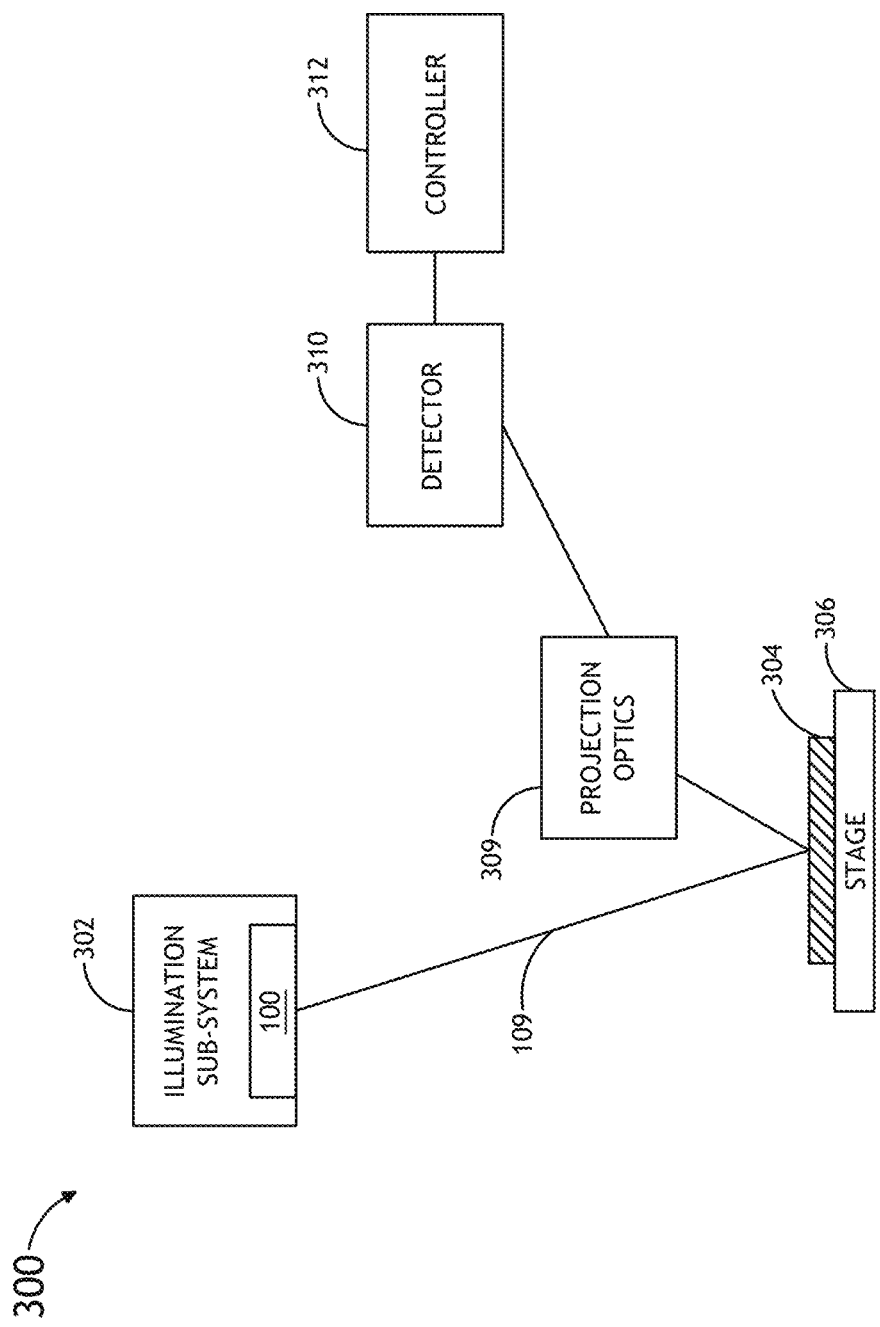
FIG. 3 is a block diagram illustrating an inspection system including a plasma-based illumination system, in accordance with an embodiment of this disclosure.

FIG. 3 illustrates a block diagram view of an inspection system 300 incorporating a plasma-based illumination source 100, in accordance with one embodiment of the present invention. In one embodiment, the system 300 includes an illumination sub-system 302. In one embodiment, the illumination sub-system 302 incorporates the EUV light generation system 100 described throughout the present invention. In another embodiment, although not shown in FIG. 3, the system 300 includes a set of illuminator optics. In one embodiment, the illuminator optics may direct illumination 109 emanating from the EUV light generation system 100 to one or more specimens 304 disposed on a specimen stage 306. For example, the one or more specimens 304 may include, but are not limited to, a wafer (e.g., semiconductor wafer). By way of another example, the one or more specimens 304 may include, but are not limited to, a reticle. In another embodiment, the system 300 includes one or more detectors 310. In another embodiment, the system 300 includes a set of projections optics 309 suitable for collecting light scatter, reflected or otherwise emanating from the specimen and directing the light to the one or more detectors (e.g., CCD, TDI-CCD, PMT and the like). In another embodiment, the system 300 includes a controller 312 for receiving and/or analyzing the measurement results from the detector 310.

In one embodiment, the inspection system 300 is configured as a wafer inspection system or a reticle inspection system. In this regard, the inspection system 300 may include any wafer or reticle inspection optical architecture known in the art suitable for operating in the EUV spectral range. It is further recognized that the inspection system 300 may be configured as an EUV mask o mask blank inspection system. EUV-based mask blank inspection is described generally in U.S. Pat. No. 8,711,346 to Stokowski, issued on Apr. 29, 2014, which is incorporated herein by reference in the entirety. EUV-based mask blank inspection is described generally in U.S. patent application Ser. No. 13/417,982 to Xiong et al., filed on Mar. 12, 2012, which is incorporated herein by reference in the entirety. EUV-based reticle inspection is generally described in U.S. patent application Ser. No. 13/905,449 to Nasser-Ghodsi et al., filed on May 30, 2013, which is incorporated herein by reference in the entirety.

In another embodiment, although not shown, the EUV light generation system 100 described throughout the present invention may be implemented with an optical lithography system. In one embodiment, the optical lithography system (not shown) may include a set of illuminator optics configured to direct output light from the EUV light generation system 100 to an EUV-compatible lithography mask (e.g., EUV reflective mask). In another embodiment, the optical lithography system includes a set of projection optics configured to receive illumination reflected from the mask and direct the reflected illumination from the mask to one or more wafers disposed on a wafer stage. The optical lithography system may include any EUV lithography system known in the art. EUV-based lithography is described generally in U.S. patent application Ser. No. 13/419,042 to Wang, filed on Mar. 13, 2012, which is incorporated herein by reference in the entirety.

Figure 4:
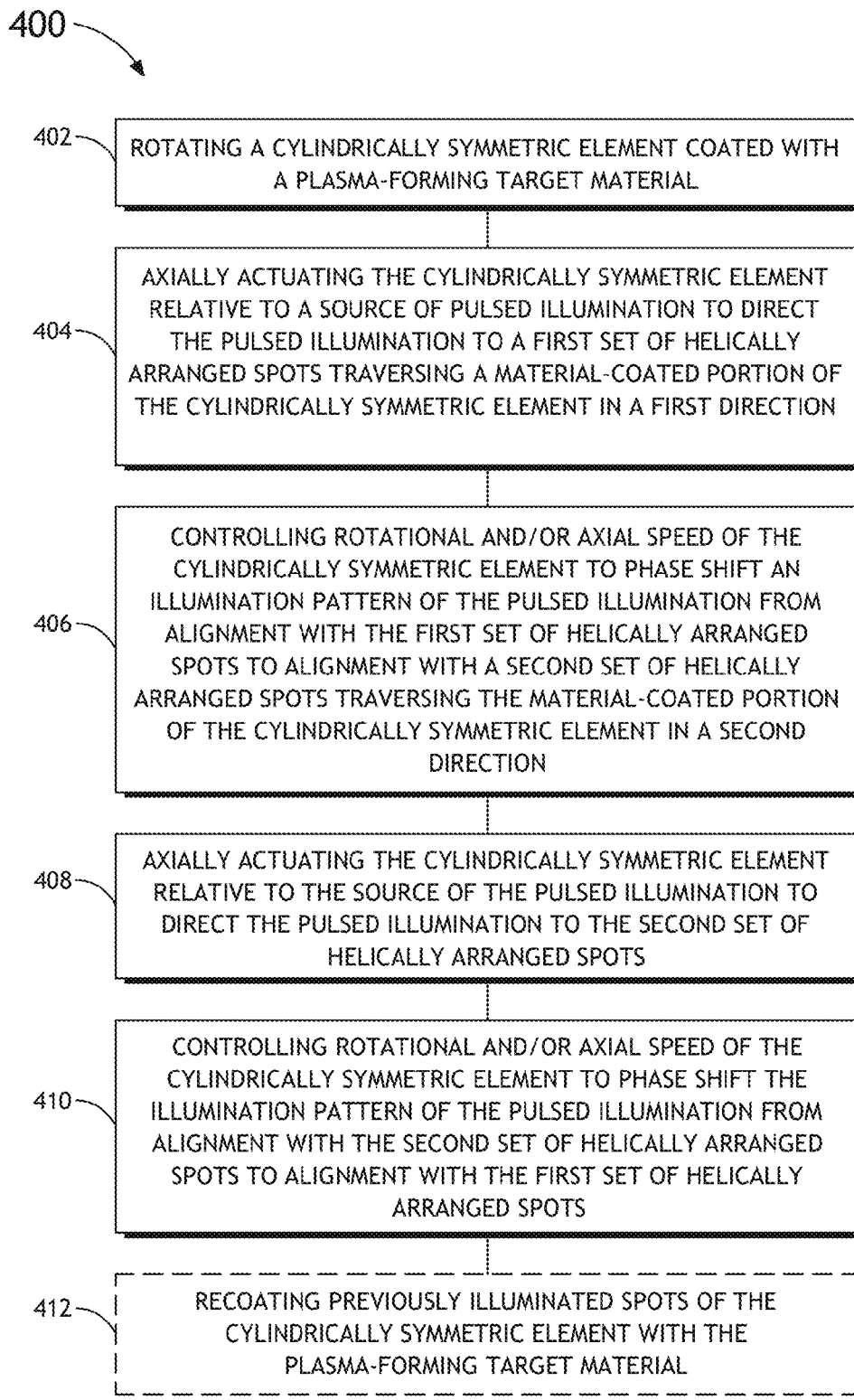
FIG. 4 is a flow diagram illustrating a method of generating plasma-based illumination by exciting a plasma-forming target material coated on a rotating cylinder, in accordance with an embodiment of this disclosure.

FIG. 4 illustrates a flow diagram depicting a method 400 for generating continuous or near-continuous plasma-based illumination, in accordance with one embodiment of the present invention.

In step 402, a cylindrically-symmetric element at least partially coated with a plasma-forming target material is rotated. For example, as shown in FIG. 1, a rotatable cylinder 102 may be rotated. For instance, the rotatable cylinder may be rotated with a rotating stage or drive coupled to a cylindrical element via shaft 113.

In step 404, the cylindrically-symmetric element is axially actuated in order to direct pulsed illumination to a first set of helically-arranged spots traversing a material-coated portion of the cylindrically-symmetric element in a first direction. For example, as shown in FIGS. 1 and 2, a pulsed illumination source 104 may direct pulsed illumination 105 to the surface of the rotating and/or axially actuated (e.g., actuated via actuator 110) cylinder 102 such that the illumination impinges on the material-coated portion of the cylinder 102 at each of a first set of helically-arranged spots 202 along a first direction 203.

In step 406, rotational speed and/or axial speed of the rotating cylinder is controlled in order to phase shift an illumination pattern of the pulsed illumination from alignment with the first set of helically-arranged spots to alignment with the second set of helically-arranged spots. For example, as shown in FIGS. 1 and 2, the controller 114 may direct a rotational control element (e.g., rotational stage, drive and the like) of the rotating cylinder 102 and/or the actuator 110 to shift the cylinder 102 from the first helical pattern 202 to a second return helical pattern 204.

In step 408, the cylindrically-symmetric element is axially actuated in order to direct pulsed illumination to a second set of helically-arranged spots traversing a material-coated portion of the cylindrically-symmetric element in a second direction. For example, as shown in FIGS. 1 and 2, a pulsed illumination source 104 may direct pulsed illumination 105 to the surface of the rotating and/or axially actuated (e.g., actuated via actuator 110) cylinder 102 such that the illumination impinges on the material-coated portion of the cylinder 102 at each of a second set of helically-arranged spots 204 along a second direction 205.

In step 410, rotational speed and/or axial speed of the rotating cylinder is controlled in order to phase shift the illumination pattern of the pulsed illumination from alignment with the second set of helically-arranged spots to alignment with the first set of helically-arranged spots. For example, as shown in FIGS. 1 and 2, the controller 114 may direct a rotational control element (e.g., rotational stage, drive and the like) of the rotating cylinder 102 and/or the actuator 110 to shift the cylinder 102 from the second helical pattern 204 to the first helical pattern 202.

In a further step 412, the previously-illuminated spots of the cylindrically-symmetric element are recoated with the plasma forming material. For example, as shown in FIG. 1, after exposure to a illumination 105 for the pulsed illumination source 104, the material source 112 may recoat the rotating cylinder 102 with the selected plasma-forming material (e.g., xenon), allowing the spots of the first and second helical patterns described previously herein to be re-exposed to illumination 105 on one or more subsequent passes.

While the present disclosure has focused on the generation of continuous or near-continuous illumination via a rotating cylinder coated with a plasma-forming material, it is recognized herein that the rotational architecture presented herein may be extended to provide continuous or near-continuous writing and/or probing of information maintained on a cylinder. Further, the rotational architecture presented herein may be extended to provide continuous or near-continuous analysis of the responsiveness of one or more selected materials to light exposure.

Figure 5:
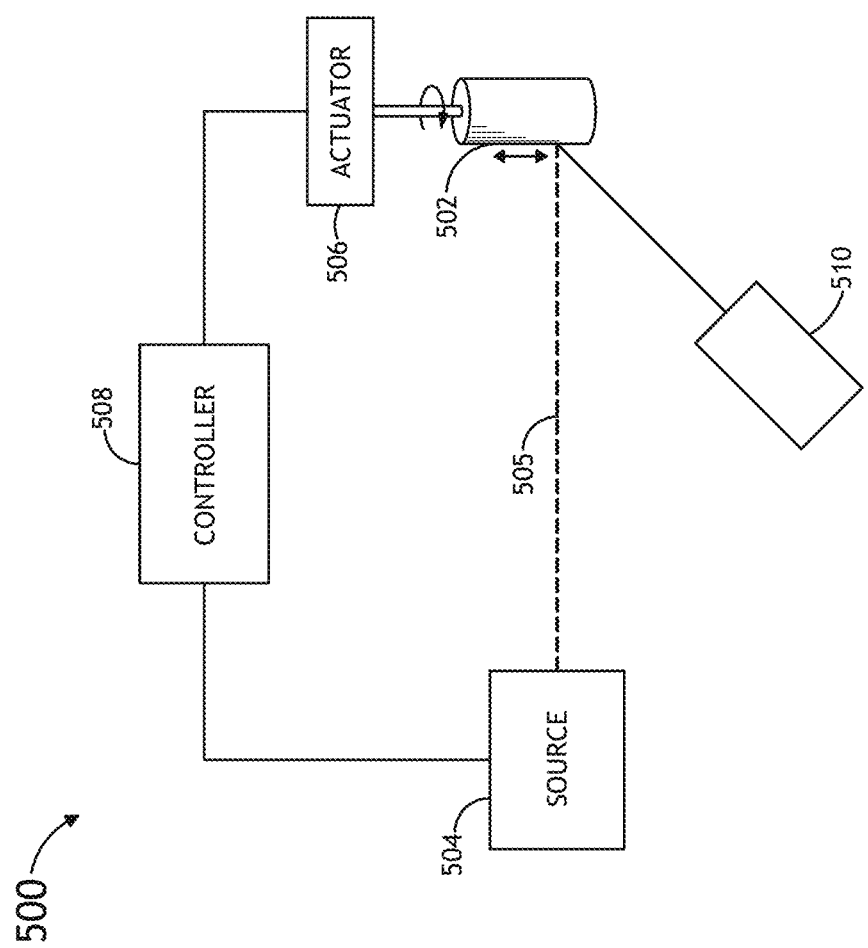
FIG. 5 is a block diagram illustrating a system for probing an information- or material-bearing cylinder, in accordance with an embodiment of this disclosure.

FIG. 5 illustrates a block diagram view of a system 500 suitable for providing continuous or near-continuous writing and/or reading of information on a cylinder, in accordance with one embodiment of the present invention. It is noted herein that the various embodiments and examples described in the context of system 100 and method 400 should be interpreted to extend to system 500. In particular, the rotational and axial control used to map out the various helical patterns of FIG. 2 should be interpreted to be implementable by system 500 in the context of writing, reading and/or rewriting information in a material disposed on the surface of a rotatable cylinder 502.

In one embodiment, the controller 508 of system 500 is configured to control the actuation (e.g., via actuator 506) and the rotation (e.g., rotational stage/motor) of the cylinder 502 to in order to scan the illumination beam 505 across the rotating and/or axially translating cylinder 502 in a selected pattern or patterns. In one embodiment, the controller 508 may control the motion of the cylinder 502 such that the light source 504 probes a first set of helically-arranged spots traversing an information- or material-bearing portion of the rotating cylinder 502 in a first direction (e.g., direction 203 as in FIG. 2). In another embodiment, the controller 508 may control the motion of the cylinder 502 such that the light source 504 probes a second set of helically-arranged spots traversing the information- or material-bearing portion of the rotating cylinder in a second direction (e.g., direction 205 as in FIG. 2). In another embodiment, the first set of helically-arranged spots and the second set of helically-arranged spots are non-overlapping. In this regard, the pulsed output of the light source 504 may be synced to the spots in the first and/or second set of helically-arranged spots. It is noted herein that the sets of helically-arranged spots of information may be formed in a material coating of the cylinder in accordance to the patterns depicted in FIG. 2. In turn, those spots may be interrogated or 'read' by the source 504 and a corresponding detector 510.

In one embodiment, the light source 504 may include a laser configured to switch 'bits' arranged at the various spots of the helical patterns ON and/or OFF. It is noted herein that any data writing/reading/re-writing scheme using laser illumination known in the art is suitable for implementation in system 500. In another embodiment, the rotatable cylinder 502 is configured such the system 500 may record information at the various spots 202, 204 of the first and/or second helical patterns for a selected time period (e.g., 1 minute to 1000 minutes). In this regard, information may be stored in a downward stroke and a corresponding upward stroke since the spots of the downward stroke (e.g., first helical pattern) do not overlap with the spots of the upward stroke (e.g., second helical pattern). In one embodiment, the probed spots on the cylinder 102 may be reconditioned with (rewritten or overwritten) with additional information or material. Once an entire cycle is complete, the light source 504 may overwrite information to the spots of the first helical pattern and second helical pattern. The size of the rotatable cylinder 502, along with the actuation and rotational speed are selected such that the overwriting process does not begin until the selected information recording cycling time is complete. For example, the size of the rotatable cylinder 502, the actuation speed and rotational speed may be selected so that a first recording cycle lasts a selected time (e.g., 30 minutes). After this selected time elapses the illumination 505 begins to retrace the spots of the first helical pattern (and then the second helical pattern), thereby overwriting the previously written information.

In another embodiment, the first set of helically-arranged spots traversing a reconditioned portion of the rotating cylinder 102 in the first direction (e.g., similar to direction 203) may be 're-probed' using the light source 504 and detector 510. In another embodiment, the second set of helically-arranged spots traversing a reconditioned portion of the rotating cylinder 102 in the second direction (e.g., similar to direction 205) may be 're-probed' using the light source 504 and detector 510.

Figure 6:
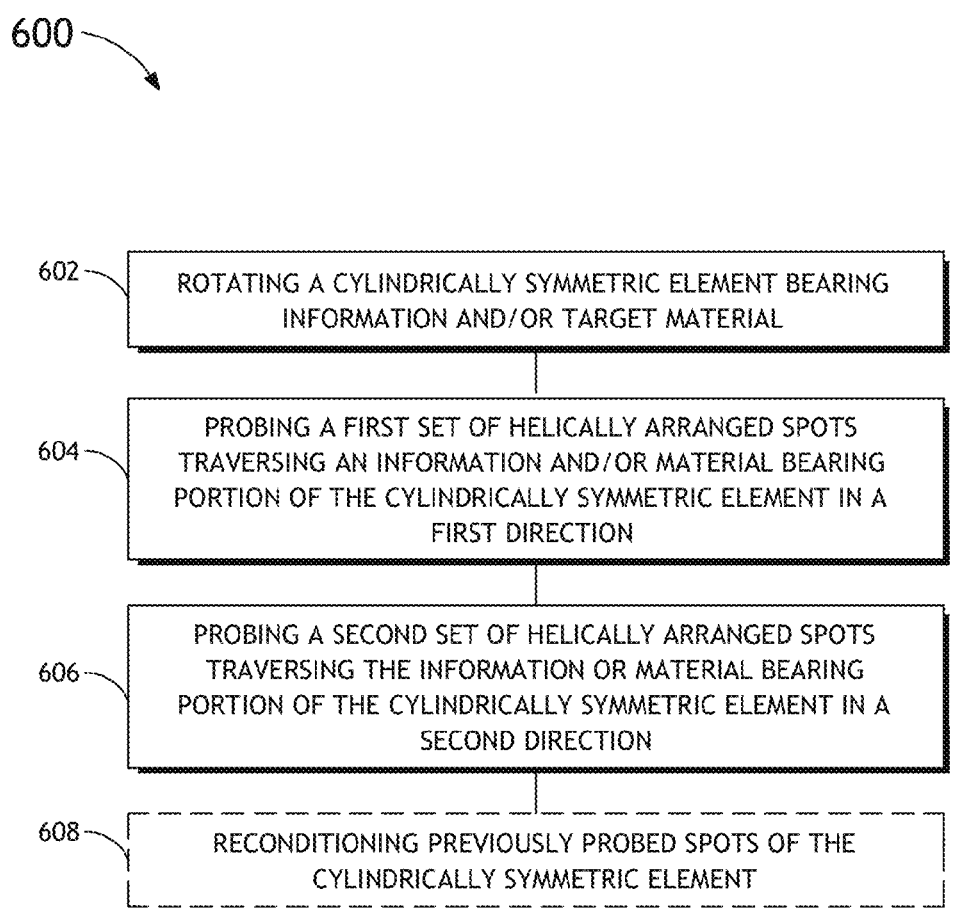
FIG. 6 is a flow diagram illustrating a method of probing an information- or material-bearing cylinder, in accordance with an embodiment of this disclosure.

FIG. 6 illustrates a flow diagram depicting a method 600 for continuously or near-continuously probing an information- or material-bearing cylinder, in accordance with one embodiment of the present invention.

In step 602, a cylindrically-symmetric element at least partially bearing information and/or a target material is rotated. For example, as shown in FIG. 5, a rotatable cylinder 502 bearing information and/or a target material may be rotated. For instance, the rotatable cylinder may be rotated with a rotating stage or drive coupled to a cylindrical element via a shaft.

In step 604, a first set of helically-arranged spots traversing an information- and/or material-bearing portion of the cylindrically-symmetric element is probed in a first direction. For example, as shown in FIGS. 5 and 2, an illumination source 504 (e.g., pulsed illumination source) may direct illumination 505 (e.g., pulsed illumination) to the information and/or target material bearing surface of the rotating and/or axially actuated (e.g., actuated via actuator 506) cylinder 502 such that the illumination probes (e.g., reads, writes and/or rewrites) the cylinder surface at the first set of helically-arranged spots 202 along a first direction 203.

In step 606, a second set of helically-arranged spots traversing an information- and/or material-bearing portion of the cylindrically-symmetric element is probed in a second direction. For example, as shown in FIGS. 5 and 2, an illumination source 504 (e.g., pulsed illumination source) may direct illumination 505 (e.g., pulsed illumination) to the information and/or target material bearing surface of the rotating and/or axially actuated (e.g., actuated via actuator 506) cylinder 502 such that the illumination probes (e.g., reads, writes and/or re-writes) the cylinder surface at the second set of helically-arranged spots 204 along a second direction 205.

In a further step 608, previously-probed spots of the cylindrically-symmetric element are reconditioned. For example, upon writing and/or reading information to spots of the first and/or second helical patterns, the spots may be reconditioned. For instance, upon writing and/or reading information to spots of the first and/or second helical patterns, the information stored at one or more of the spots of the first and/or second helical patterns may be erased (e.g., thermally erased via exposure to high energy via light source 504). In another instance, upon writing and/or reading information to spots of the first and/or second helical patterns, the new or additional information may be rewritten at one or more of the spots of the first and/or second helical patterns.

Figure 7:
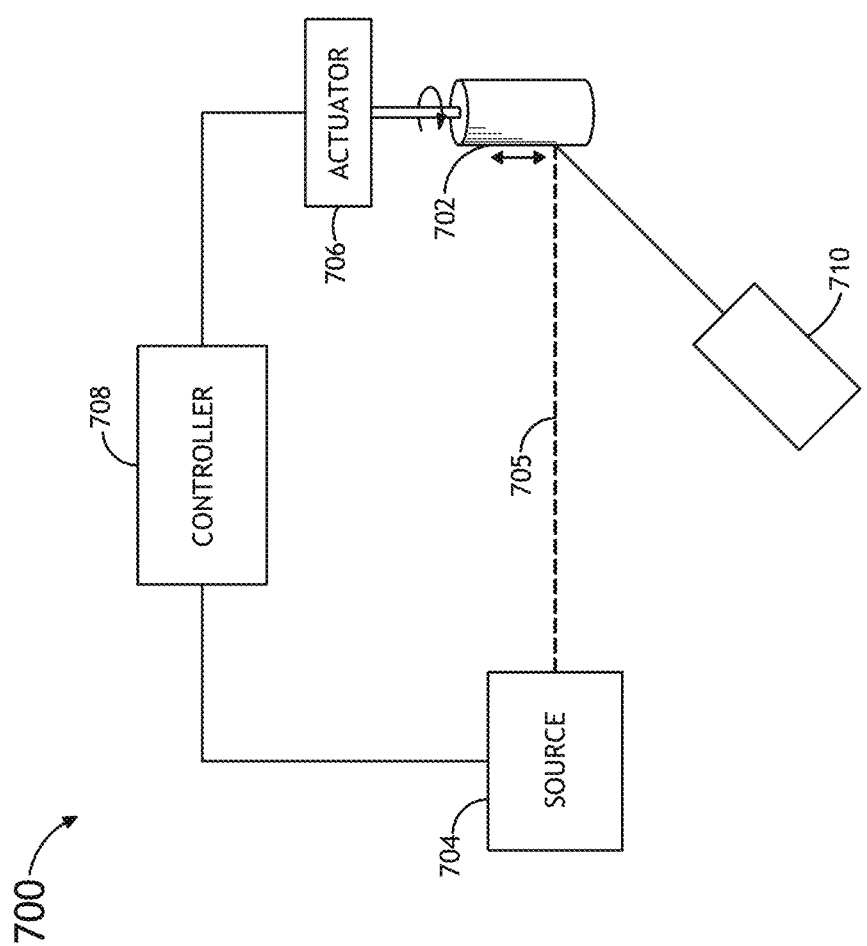
FIG. 7 is a block diagram illustrating a system for measuring the response of a selected material to illumination of varying exposure energies, in accordance with an embodiment of this disclosure.

FIG. 7 illustrates a block diagram view of a system 700 suitable for continuous or near-continuous analysis of the responsiveness of one or more selected materials to light exposure, in accordance with one embodiment of the present invention. It is noted herein that the various embodiments and examples described in the context of systems 100 and 500 and methods 400 and 600 should be interpreted to extend to system 700. In particular, the rotational and axial control used to map out the various helical patterns of FIG. 2 should be interpreted to be implementable by system 700 in the context of exposing various portions of a material disposed on the surface of a rotatable cylinder 702 to light.

In one embodiment, the controller 708 of system 700 is configured to control the actuation (e.g., via actuator 706) and the rotation (e.g., rotational stage/motor) of the cylinder 702 to in order to scan the illumination beam 705 across the rotating and/or axially translating cylinder 702 in a selected pattern or patterns. In one embodiment, the controller 708 may control the motion of the cylinder 702 such that the light source 704 exposes each of a first set of helically-arranged spots traversing a material bearing portion of the rotating cylinder 702 in a first direction (e.g., direction 203 as in FIG. 2) with one or more selected levels of energy. In another embodiment, the controller 708 may control the motion of the cylinder 702 such that the light source 704 exposes each of a second set of helically-arranged spots traversing a material bearing portion of the rotating cylinder 702 in a second direction (e.g., direction 205 as in FIG. 2) with one or more selected levels of energy. In another embodiment, the first set of helically-arranged spots and the second set of helically-arranged spots are non-overlapping. In this regard, the output of the light source 704 may expose multiple locations of a selected material to determine how the selected material reacts to a given high-intensity energy application. Further, system 700 may be used to determine how a selected material 'relaxes' or returns to its original state over a selected time. In another embodiment, the various spots of the cylinder 702 may be re-exposed to the illumination 705 (e.g., high intensity light) by the light source 704. It is further noted herein that the size of the rotating cylinder 702 and the rotational and axial speed of the cylinder 702 may be selected (and adjusted) to dictate the time period before the various spots are re-exposed to illumination 705 from the light source 704.

In another embodiment, the system 700 may include a detector 710 configured to collect and analyze one or more characteristics associated (e.g., intensity, spectral features and the like) with light that is scattered or reflected from the exposed portions of the cylinder. In this manner, a large number of measurements of a selected material interacting with varying levels of energy (e.g., varying across the spots of the first and/second helical patterns) may be collected. In turn, the relaxation characteristic of each of the spots (exposed to varying levels of energy) may be examined. It is noted herein that this allows the system 700 to generate a statistically large number of samples. For example, such a configuration may be implemented to analyze the response (e.g., time of efficacy) of a selected laser shielding material exposed to illumination from a pulsed laser.

Those having skill in the art will appreciate that there are various vehicles by which processes and/or systems and/or other technologies described herein can be embodied (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, programmable logic devices, ASICs, analog or digital controls/switches, microcontrollers, or computing systems. A computing system may include, but is not limited to, a personal computing system, mainframe computing system, workstation, image computer, parallel processor, or any other device known in the art. In general, the terms "computing system" and "controller" (e.g., controller 114, controller 312, controller 508 and 708) are broadly defined to encompass any device having one or more processors, which execute program instructions from a carrier medium. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a solid state memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A method of generating continuous or near-continuous plasma-based illumination comprising:
   rotating a cylinder at least partially coated with a plasma-forming target material;
   directing pulsed illumination to a first set of helically-arranged spots traversing a material-coated portion of the rotating cylinder in a first direction; and
   directing the pulsed illumination to a second set of helically-arranged spots traversing the material-coated portion of the rotating cylinder in a second direction, the pulsed illumination being suitable for exciting the plasma-forming target material.

2. The method of claim 1, wherein the plasma-based illumination comprises:
   extreme ultraviolet (EUV) light.

3. The method of claim 1, further comprising:
   recoating previously-illuminated spots of the rotating cylinder with the plasma-forming target material.

4. The method of claim 3, further comprising:
   redirecting the pulsed illumination to the first set of helically-arranged spots traversing a recoated portion of the rotating cylinder in the first direction; and
   redirecting the pulsed illumination to the second set of helically-arranged spots traversing the recoated portion of the rotating cylinder in the second direction.

5. The method of claim 1, further comprising:
   axially actuating the rotating cylinder relative to a source of the pulsed illumination to direct the pulsed illumination to the first set of helically-arranged spots traversing the material-coated portion of the rotating cylinder in the first direction; and
   axially actuating the rotating cylinder relative to the source of the pulsed illumination to direct the pulsed illumination to the second set of helically-arranged spots traversing the material-coated portion of the rotating cylinder in the second direction.

6. The method of claim 5, further comprising:
   during a change from the first direction of the pulsed illumination to the second direction of the pulsed illumination, controlling at least one of a rotational speed and an axial speed of the rotating cylinder to phase shift an illumination pattern of the pulsed illumination from alignment with the first set of helically-arranged spots to alignment with the second set of helically-arranged spots.

7. The method of claim 1, wherein the first set of helically-arranged spots and the second set of helically-arranged spots are non-overlapping.

8. The method of claim 1, wherein the first set of helically-arranged spots comprises spots that are spaced at least twice as far apart as a predetermined threshold spacing, the threshold spacing being a minimum distance between adjacent spots required to avoid exposure of non-targeted portions of the rotating cylinder by the pulsed illumination.

9. The method of claim 8, wherein the threshold spacing is based upon at least one of a rotational speed of the rotating cylinder, a diameter of the rotating cylinder, a pulse-rate of the pulsed illumination, a length of the material-coated portion of the rotating cylinder, and a deposition rate of the plasma-forming target material upon the rotating cylinder.

10. A system for generating continuous or near-continuous plasma-based illumination comprising:
    a rotatable, cylindrically-symmetric element at least partially coated with plasma-forming target material;
    a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; and
    one or more collection optical elements configured to receive illumination emanated from a plasma generated in response to the excitation of the plasma-forming target material and further configured to direct the illumination towards an intermediate focal point.

11. The system of claim 10, wherein the rotatable, cylindrically-symmetric element comprises:
    a cylinder.

12. The system of claim 10, further comprising:
    a material source configured to recoat previously-illuminated portions of the rotatable, cylindrically-symmetric element with the plasma-forming target material.

13. The system of claim 10, further comprising:
    one or more actuators configured to actuate the rotatable cylinder along an axial direction.

14. The system of claim 13, further comprising:
    a controller in communication with the one or more actuators, the controller including one or more processors configured to execute program instructions configured to cause the one or more actuators to:
        axially actuate the rotatable, cylindrically-symmetric element relative to the pulsed illumination source to direct the pulsed illumination to the first set of helically-arranged spots traversing the material-coated portion of the rotatable, cylindrically-symmetric element in the first direction; and
        axially actuate the rotatable, cylindrically-symmetric element relative to the pulsed illumination source to direct the pulsed illumination to the second set of helically-arranged spots traversing the material-coated portion of the rotatable, cylindrically-symmetric element in the second direction.

15. The system of claim 14, wherein the controller is further configured to:
    during a change from the first direction of the pulsed illumination to the second direction of the pulsed illumination, control at least one of a rotational speed and an axial speed of the rotatable, cylindrically-symmetric element to phase shift an illumination pattern of the pulsed illumination from alignment with the first set of helically-arranged spots to alignment with the second set of helically-arranged spots.

16. The system of claim 10, wherein the first set of helically-arranged spots and the second set of helically-arranged spots are non-overlapping.

17. The system of claim 10, wherein at least one of the first set of helically-arranged spots and the second set of helically-arranged spots includes spots that are spaced at least twice as far apart as a predetermined threshold spacing, the threshold spacing being a distance between adjacent spots required to avoid exposure of non-targeted portions of the rotatable, cylindrically-symmetric element by the pulsed illumination.

18. The system of claim 17, wherein the threshold spacing is based upon at least one of a rotational speed of the rotatable, cylindrically-symmetric element, a diameter of the rotatable, cylindrically-symmetric element, a pulse-rate of the pulsed illumination, a length of the material-coated portion of the rotatable, cylindrically-symmetric element, and a deposition rate of the plasma-forming target material upon the rotatable, cylindrically-symmetric element.

19. An optical inspection system comprising:
    an illumination sub-system including:
        a rotatable, cylindrically-symmetric element at least partially coated with plasma-forming target material;
        a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; and
        one or more collection optical elements configured to collect illumination emanated from a plasma generated in response to the excitation of the plasma-forming target material;
    a set of illuminator optics configured to direct illumination from the one or more collection optical elements to one or more specimens;
    a detector; and
    a set of projection optics configured to receive illumination from the surface of the one or more specimens and direct the illumination from the one or more specimens to the detector.

20. The optical inspection system of claim 19, wherein the optical inspection system is configured as a wafer inspection system.

21. The optical inspection system of claim 19, wherein the optical inspection system is configured as a reticle inspection system.

22. The optical inspection system of claim 19, wherein the illumination includes extreme ultraviolet light.

23. An optical lithography system comprising:
    an illumination sub-system including:
        a rotatable, cylindrically-symmetric element at least partially coated with plasma-forming target material;
        a pulsed illumination source configured to direct pulsed illumination to a first set of helically-arranged spots traversing a material-coated portion of the rotatable, cylindrically-symmetric element in a first direction and further configured to direct the pulsed illumination to a second set of helically-arranged spots traversing the material-coated portion of the rotatable, cylindrically-symmetric element in a second direction, the pulsed illumination being suitable for exciting the plasma-forming target material; and one or more collection optical elements configured to collect illumination emanated from a plasma generated in response to the excitation of the plasma-forming target material;

a set of illuminator optics configured to direct collected illumination to a mask; and a set of projection optics configured to receive illumination reflected from the mask and direct the reflected illumination from the mask to one or more wafers.

24. The optical lithography system of claim 23, wherein the illumination includes extreme ultraviolet light.

25. A method of continuously or near-continuously probing an information- or material-bearing cylinder, comprising:

rotating the cylinder;

probing a first set of helically-arranged spots traversing an information- or material-bearing portion of the rotating cylinder in a first direction; and probing a second set of helically-arranged spots traversing the information- or material-bearing portion of the rotating cylinder in a second direction, wherein the first set of helically-arranged spots and the second set of helically-arranged spots are non-overlapping.

26. The method of claim 25, further comprising:

reconditioning previously-probed spots of the rotating cylinder with additional information or material.

27. The method of claim 26, further comprising:

reprobing the first set of helically-arranged spots traversing a reconditioned portion of the rotating cylinder in the first direction; and reprobing the second set of helically-arranged spots traversing the reconditioned portion of the rotating cylinder in the second direction.

28. The method of claim 25, further comprising:

axially actuating the rotating cylinder relative to a probe source to probe the first set of helically-arranged spots traversing the information- or material-bearing portion of the rotating cylinder in the first direction; and axially actuating the rotating cylinder relative to the probe source to probe the second set of helically-arranged spots traversing the information- or material-bearing portion of the rotating cylinder in the second direction.

29. The method of claim 28, further comprising:

during a change from the first probing direction to the second probing direction, controlling at least one of a rotational speed and an axial speed of the rotating cylinder to phase shift a probing pattern from alignment with the first set of helically-arranged spots to alignment with the second set of helically-arranged spots.

30. The method of claim 25, wherein the first set of helically-arranged spots comprises spots that are spaced at least twice as far apart as a predetermined threshold spacing, the threshold spacing being a minimum distance between adjacent spots required to avoid probing of non-targeted portions of the rotating cylinder.

* * * * *